(12) United States Patent
Zimdars et al.

(10) Patent No.: US 10,215,696 B2
(45) Date of Patent: Feb. 26, 2019

(54) SYSTEM FOR DETERMINING AT LEAST ONE PROPERTY OF A SHEET DIELECTRIC SAMPLE USING TERAHERTZ RADIATION

(71) Applicant: Picometrix, LLC, Ann Arbor, MI (US)

(72) Inventors: David Zimdars, Ann Arbor, MI (US); Jeffrey S. White, Manchester, MI (US); Steven Williamson, Ann Arbor, MI (US); Irl Duling, Ann Arbor, MI (US)

(73) Assignee: PICOMETRIX, LLC, Ann Arbor, MI (US)

( * ) Notice: Subject to any disclaimer, the term of this patent is extended or adjusted under 35 U.S.C. 154(b) by 0 days.

(21) Appl. No.: 15/154,040

(22) PCT Filed: Nov. 14, 2014

(86) PCT No.: PCT/US2014/065677
§ 371 (c)(1),
(2) Date: May 13, 2016

(87) PCT Pub. No.: WO2015/073807
PCT Pub. Date: May 21, 2015

(65) Prior Publication Data
US 2017/0023469 A1 Jan. 26, 2017

Related U.S. Application Data

(60) Provisional application No. 61/904,787, filed on Nov. 15, 2013.

(51) Int. Cl.
*G01N 21/86* (2006.01)
*G01N 21/3586* (2014.01)
(Continued)

(52) U.S. Cl.
CPC ......... *G01N 21/3586* (2013.01); *G01B 11/06* (2013.01); *G01N 21/21* (2013.01);
(Continued)

(58) Field of Classification Search
CPC .... G01N 21/3586; G01N 21/41; G01N 21/21; G01N 2021/8663; G01N 2201/08; G01N 2201/0697; G01N 2201/06113
See application file for complete search history.

(56) References Cited

U.S. PATENT DOCUMENTS 4,955,720 A * 9/1990 Blecha ................. D21G 9/0027
162/198
5,604,581 A * 2/1997 Liu ..................... G01B 11/0625
356/632
(Continued)

FOREIGN PATENT DOCUMENTS

EP 1 640 709 A1 3/2006
EP 2 781 911 A1 9/2014
(Continued)

OTHER PUBLICATIONS

European Search Report dated Jun. 22, 2017.

*Primary Examiner* — David P Porta
*Assistant Examiner* — Djura Malevic
(74) *Attorney, Agent, or Firm* — Brinks Gilson & Lione (57) ABSTRACT

A system for determining at least one property of a sheet dielectric sample using terahertz radiation includes at least one terahertz transmitter configured to output a pulse of terahertz radiation, a terahertz receiver configured to receive at least a portion of the pulse of terahertz radiation, wherein the terahertz receiver is configured to output a measured waveform based on the terahertz radiation received by the terahertz receiver, and a control unit in communication with the terahertz receiver. Wherein the control unit is configured to choose at least one region of interest of the measured waveform, compare the at least one region of interest of the measured waveform to a model waveform, vary at least one
(Continued)

parameter of a model waveform to minimize the difference between the model waveform and the measured waveform.

18 Claims, 4 Drawing Sheets

(51) Int. Cl.
    *G01N 21/3581* (2014.01)
    *G01B 11/06* (2006.01)
    *G01N 21/21* (2006.01)
    *G01N 21/41* (2006.01)
    *G01N 21/3559* (2014.01)

(52) U.S. Cl.
    CPC ..... *G01N 21/3559* (2013.01); *G01N 21/3581* (2013.01); *G01N 21/41* (2013.01); *G01N 21/86* (2013.01); *G01N 2021/8663* (2013.01); *G01N 2201/0697* (2013.01); *G01N 2201/06113* (2013.01); *G01N 2201/08* (2013.01)

(56) References Cited

U.S. PATENT DOCUMENTS

| | | | |
|---|---|---|---|
| 5,640,244 A * | 6/1997 | Hellstrom | G01B 11/26 250/559.16 |
| 6,242,739 B1 * | 6/2001 | Cherkassky | G01B 11/0641 250/339.08 |
| 7,199,884 B2 * | 4/2007 | Jasinski | G01B 11/0691 356/429 |
| 7,681,434 B2 * | 3/2010 | Ouchi | G01N 21/3581 250/338.1 |
| 8,344,324 B2 * | 1/2013 | Kasai | G01N 21/3586 250/341.1 |
| 9,423,791 B2 * | 8/2016 | Van Mechelen | G05B 19/41875 |
| 2003/0156293 A1 * | 8/2003 | Kazuhiko | G01N 21/17 356/446 |
| 2006/0197021 A1 * | 9/2006 | Ouchi | G01N 21/3581 250/343 |
| 2006/0237156 A1 * | 10/2006 | Shakespeare | G01N 21/8806 162/198 |
| 2007/0195921 A1 * | 8/2007 | Ouchi | G01N 22/00 378/1 |
| 2007/0252604 A1 * | 11/2007 | Ouchi | G01N 21/3581 324/639 |
| 2008/0037031 A1 * | 2/2008 | Cole | G01N 21/55 356/601 |
| 2009/0101297 A1 * | 4/2009 | Jez | G01N 21/23 162/198 |
| 2009/0128799 A1 | 5/2009 | MacHattie et al. | |
| 2010/0024999 A1 * | 2/2010 | Haran | D21F 7/003 162/198 |
| 2010/0282970 A1 * | 11/2010 | Haran | G01J 3/02 250/339.07 |
| 2012/0304756 A1 | 12/2012 | White et al. | |
| 2013/0204577 A1 | 8/2013 | Savard et al. | |

FOREIGN PATENT DOCUMENTS

| | | |
|---|---|---|
| JP | 2011503583 A | 1/2011 |
| JP | 2011530070 A | 12/2011 |
| JP | 2013507640 A | 3/2013 |
| JP | 2013536422 A | 9/2013 |
| WO | WO 2004113885 A1 | 12/2004 |

* cited by examiner

SYSTEM FOR DETERMINING AT LEAST ONE PROPERTY OF A SHEET DIELECTRIC SAMPLE USING TERAHERTZ RADIATION

CROSS REFERENCE TO RELATED APPLICATIONS

This application is a nationalization of PCT Serial No. PCT/US2014/065677, filed Nov. 14, 2014 which claims benefit of U.S. Provisional Application Ser. No. 61/904,787, filed Nov. 15, 2013.

BACKGROUND

1. Technical Field Text

This application relates to systems for determining material properties of a sheet dielectric and more particularly to systems for determining material properties of a sheet dielectric using terahertz radiation.

2. Background Information

Sheet dielectrics, such as paper may have one or more material properties that may need to be determined during the manufacture thereof. For example, paper is a thin sheet material typically composed of compressed fibers. The material is produced by pressing together moist fibers into a sheet of a usually uniform thickness and then drying the material. The fibers are usually cellulose pulp made from wood, fabrics, or other vegetable matter. Additives may be incorporated such as chalk, clay, and titanium dioxide. "Sizing" additives may be incorporated to modify the surface absorbency to ink or water, for example, to prevent "bleeding."

Papers are characterized by several physical parameters. The thickness of paper is referred to the "caliper". An approximate range of thicknesses is 70 microns (2.76 mils) to 180 microns (7.1 mils). A micron is 0.001 millimeter. A mil is 0.001 in. Cardstock and cardboard may be thicker. Paper is also characterized by its "basis weight" which is a density related to the mass per unit area, typically grams/meter$^2$. A typical range of printing paper is 60 g to 120 g. Heavier paper is considered card stock. The mass per unit area may also be expressed as the weight of a ream of 500 sheets of a standard size of paper. The density of paper (basis weight/caliper) ranges from about 250 kg/m$^3$ to 1,500 kg/m$^3$. Typical printing paper is 800 kg/m$^3$.

Industrial papermaking machines produce a continuous sheet of paper, known as the paper web, starting with wet pulp and ending with the finished dry paper roll. The first step is to deposit the pulp slurry in the forming section. The forming section established the orientation of layup of the fibers, called the "formation." The press section squeezes the paper web through larger rollers to remove much of the water. The drying section passes the paper web through a serpentine of heated rollers. The water content is reduced to a range of 2% to 10% (typically about 6%) depending on the type of paper. The percentage water content is defined as the weight of the adsorbed water alone divided by the total weight of the water and the paper. The calendar section smoothes the dried paper by pressing the sheet with heavy polished steel rollers.

Paper making machines are typically instrumented with one or more gauges, also referred to as sensors, to measure one or more of the typical characteristics such as caliper, basis weight, formation, and water content. These gauges may be placed after the calendar section to measure the finished properties of the paper; or earlier in the forming, press, and/or drying sections. These properties are used to both characterize the paper and to provide feedback to adjust the paper making machine to produce paper with the desired characteristics.

The most rapid feedback is achieved when the gauges are mounted on-line to directly measure the paper web as it moves through the machine. Ideally, on-line measurement gauges should not disturb or contact the paper web. This requirement restricts the technology used in the gauges to that which does not consume or alter the sample during the measurement process. Historically, basis weight was measured by radiological source gauges, such as beta-gauges, which measures the attenuation of the flux of radiation through the paper. Formation may be measured by vision systems, such as cameras. Water content historically was measured by near infrared ("NIR") spectroscopy; or measured by microwaves in a resonant cavity. Caliper was (and is) difficult to measure, although gauges employing feelers, laser displacement, or chromatic aberration analysis have some success. On-line gauges may be used for off-line laboratory analysis of paper samples.

The web width of paper-making machines may be several meters wide. However, most on-line gauges most readily only measure a single point or small area of the paper-web at a time. To make measurements along the entire width, the on-line gauges are typically mounted on a motion-control gantry suspended above (and/or below) the width of the web. The motion gantry is programmed to move the gauges laterally across the width of the web (called the "cross-direction" or CD) while the paper web moves underneath the gantry at a steady rate (called the "machine-direction" or MD). Often more than one gauge (sensor) is mounted on the same carriage traversing the gantry. The gantry typically has a position encoder to determine the location of the gauge carriage over the paper web. The gauges on the gantry then essentially trace a zigzag pattern over the paper.

Many types of sensors, most notably beta-gauges, require gauge components, such as the emitter and detector, to be mounted above and below the web. In this case a second gantry is used and the motion of the second gauge carriage is synchronized to the primary gantry carriage. Certain types of gauges must move "off-web" occasionally for calibration or normalization, measuring only air. Many gauges are augmented by temperature, air pressure, and air humidity sensors that may be used to correct the measured parameters for change in the gauge calibration as these environmental conditions may vary.

Historically, in order to measure multiple paper characteristic parameters on the web, the on-line measurement system requires multiple gauges, at least one of each type corresponding to each parameter. For example measurement of basis weight and measurement of water content may require both a beta gauge and a NIR gauge

BRIEF SUMMARY

A system for determining at least one property of a sheet dielectric sample using terahertz radiation may include at least one terahertz transmitter configured to output a pulse of terahertz radiation to the sheet dielectric sample, a terahertz receiver configured to receive at least a portion of the pulse of terahertz radiation from the sheet dielectric sample, wherein the terahertz receiver is configured to output a measured waveform based on the terahertz radiation received by the terahertz receiver, and a control unit in communication with the terahertz receiver and configured to receive the measured waveform from the terahertz receiver.

The measured waveform may be a time domain waveform or a frequency domain waveform.

The control unit may be configured to choose at least one region of interest of the measured waveform, compare the at least one region of interest of the measured waveform to a model waveform, vary at least one parameter of a model waveform to minimize the difference between the model waveform and the measured waveform, and determine the at least one parameter of the model waveform so that the model waveform best matches the measured waveform. The at least one parameter of the model waveform mat include the thickness of a sheet dielectric model and complex index of refraction of a sheet dielectric model. The complex index of refraction of the sheet dielectric model may be parameterized by water content and/or basis weight.

The control unit may be further configured to determine the thickness of the sheet dielectric sample by the thickness of the model waveform to best match the measured waveform. In addition the control unit may be further configured to determine the water content or basis weight of the sheet dielectric sample by varying the complex index of refraction to predict a complex index of refraction of the sheet dielectric sample.

Further objects, features and advantages of the invention will become readily apparent to persons skilled in the art after a review of the following description, with reference to the drawings and claims that are appended to and form a part of this specification.

DETAILED DESCRIPTION OF THE DRAWINGS AND THE PRESENTLY PREFERRED EMBODIMENTS

Figure 1A:
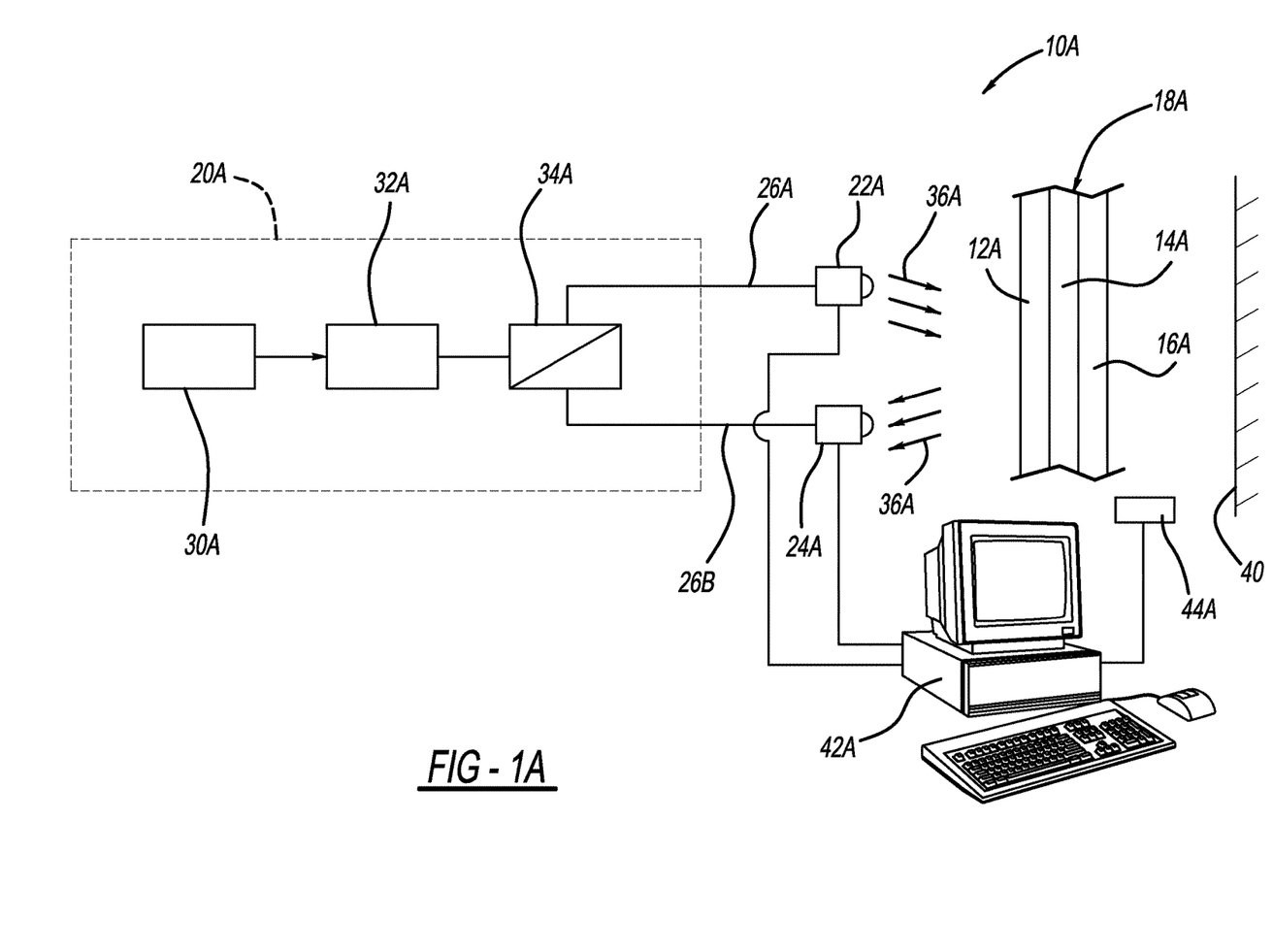
FIG. 1A illustrates a block diagram of a system for determining at least one property of a sheet dielectric sample using reflected terahertz radiation.

Referring to FIG. 1A, a system 10a for determining at least one property of a sheet dielectric sample 12a using terahertz radiation is shown. As its primary components, the system 10a includes an optical control source 20a, at least one terahertz transmitter 22a, a terahertz receiver 24a and a means 26a and 28a for providing optical signals outputted by the optical control source 20a to both the transmitter 22a and a receiver 24a.

The means 26a and 28a for providing the optical signal is such that the receiver 24a is synchronized to the transmitter 22a by optical signals emitted by the optical control source 20a. In this embodiment, the means 26a and 28a are single mode optical fibers. However, the means 26a and 28a may be multimode fibers or even a free space transmission of the optical signals from the optical control source 20a to the transmitter 22a and/or the receiver 24a. The terahertz transmitter 22a serves as the source of an electromagnetic impulse which then propagates through an optical transport, such as a series of lenses, mirrors, and windows transmitting and/or reflecting from a sample under test to be recorded by the terahertz receiver 24a. In certain cases the optical transport may be configured to convey both the terahertz pulses reflected from the sample and the pulses transmitted sample to two independent receivers or to a single receiver simultaneously or in sequence.

Generally, the optical control source 20a may take a variety of different forms. In one such embodiment, the optical control source 20a includes a laser source 30a configured to output optical pulses. Generally, the laser source 30a produces femtosecond output pulses. Optically coupled to the laser source 30a is a compensator 32a. Optical pulses emitted by the laser source 30a are provided to the compensator 32a which adds opposite sign dispersion to the optical pulses to correct for a stretching of the optical pulses as they travel through the means 26a and 28a when the means 26a and 28a are optical fibers. In a free space transmission of the optical pulses to the transmitter 22a and the receiver 24a, the compensator 32a is generally unnecessary and can be omitted. The compensator 32a and laser source 30a may be optically coupled to each other by an optical fiber or may be optically coupled to each other in a free space manner.

Once the appropriate amount of opposite sign dispersion is provided to the optical pulses by the compensator 32a, the optical pulses are provided to a splitter 34a. The splitter 34a splits the optical pulses and provides them to a first optical fiber 26a and a second optical fiber 28a. In this embodiment, the first optical fiber 26a is a single mode fiber wherein pulses split by the splitter 34a are provided to the optical fiber 26a. In like matter, the second optical fiber 28a is also an optical fiber receiving pulses split from the splitter 34a.

The optical fiber 24a is coupled to the transmitter 22a. Similarly, optical fiber 26a is optically coupled to receiver 24a. When the receiver 22a receives these optical pulses from the optical fiber 26a, the receiver 22a will output at least one pulse of terahertz radiation 36a to a sheet dielectric sample 18a. When the receiver 24a receives optical pulses from the optical fiber 28a, the receiver 24a will receive at least a portion of the pulse of terahertz radiation 38a emitted from the transmitter 22a and reflected off the sheet dielectric sample 18a. Because of this, timing is important such that the receiver 24a is synchronized to the transmitter 22a by the optical pulses traveling on optical fiber 26a and optical fiber 28a.

The transmitter 22a may generate the terahertz pulses through the action of a biased photoconductive semiconductor switch, electro-optic crystal, or some other means (e.g. four wave mixing, Fourier synthesis). A photoconductive semiconductor switch or electro-optic crystal transmitter is typically driven by an optical or near infrared femtosecond (or sub-picosecond) laser source. A photoconductive semiconductor switch emission device creates a real current in a voltage biased region of the semiconductor that flows as the laser pulse is absorbed and creates carriers in the semiconductor conduction band. The photoconductive semiconductor switch semiconductor material is usually chosen to have a (sub-) picosecond carrier lifetime. In this manner the current rises and decays in an impulse response that follows the envelope of the laser pulse. Photoconductive semiconductor switch transmitter devices typically have metallic planar antenna fabricated on the semiconductor; the antenna serve to both enhance the emission of the terahertz pulse and provide bias the absorption region. The antenna are terahertz resonant typically dipoles, bow tie, or similar, with the "feed" being a small gap between the two halves where the laser light is absorbed in the semiconductor connecting both sides of the antenna. In certain cases traditional antenna are not used and the pulse is emitted only from the acceleration of the carriers in the biased semiconductor ("Hertzian dipole"). Typical photoconductive semiconductor switch semiconductor materials include low temperature grown gallium arsenide (LT-GaAs) and radiation damaged silicon on sapphire suitable for <850 nm laser sources; and low temperature grown indium gallium arsenide (LT-InGaAs) suitable for <1060 nm and/or <1550 nm laser sources. The ultrafast laser pulses may have a higher frequency than the band gap energy. The semiconductors may be doped to modify their lifetime and/or band gap. Electro-optic crystal transmitter devices are likewise driven by similar ultrafast laser pulses; however the emission is typically due to non-linear optical rectification of the laser pulse in the crystal. Typical crystals are Zinc Telluride, Gallium Phosphide, DAST and others.

Additionally, the system 10a may also include an external reference structure 40. The external reference structure 40 may be completely reflective, such as a mirror. In this situation, radiation 38A is reflected by each layer of the sheet dielectric sample 18A but also by the external reference structure 40. Further, the system 10a may also include additional sensors 44a. These additional sensors 44a may include a near infrared sensor, an eddy current sensor, a magnetic sensor, a visible spectroscopy sensor, calipers, a nuclear magnetic resonance spectroscopy sensor, or a Raman spectroscopy sensor.

Once the radiation 38a is received by the receiver 24a, the receiver 24a generates an electrical signal which can be interpreted, scaled and/or digitized by a control unit 42a. The control unit 42a is generally electrically coupled to the receiver 24a so as to receive the electrical signals from the receiver 24a.

Figure 2:
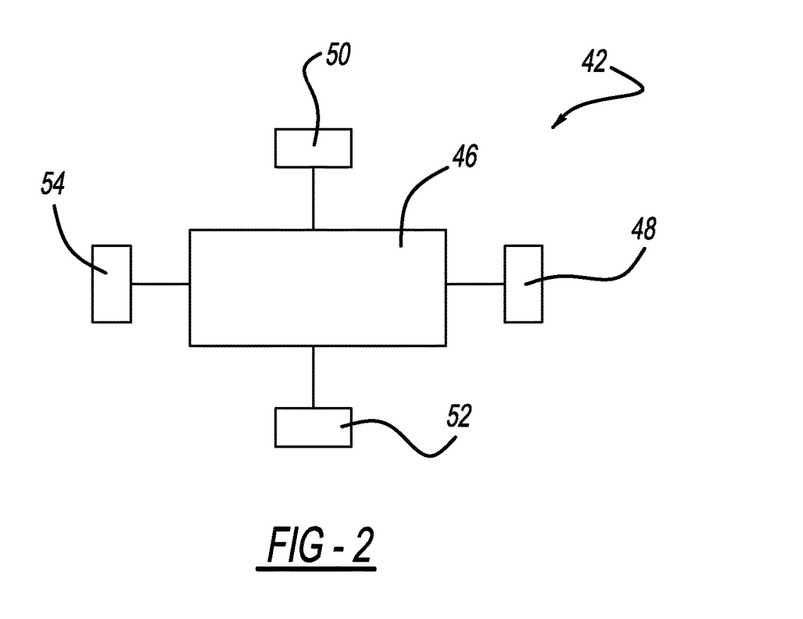
FIG. 2 illustrates a block diagram of a control unit for a system for determining at least one property of a sheet dielectric sample using terahertz radiation.

Referring to FIG. 2, in its simplest form, the control unit 42 may include a processor 46 in communication with a memory device 48. The processor 46 may be a single processor or may be multiple processors that work in concert to perform tasks. The memory device 48 may be any one of a number of different devices capable of storing digital information. For example, the memory device 48 may be a magnetic device, such as a hard drive, and optical device, such as an optical disc reader, or a solid-state device, such as flash memory. The memory device 48 may store waveforms transmitted from the receiver 24. The memory device 48 may also include instructions for configuring the processor 46 to appropriately analyze any received the waveforms as will be described later in this application.

The control unit 42 may also include an input device 50 in communication with the processor 46 for receiving input. The input device 50 may be a keyboard, a mouse, or even external storage device. The control unit 42 may also include an output device 52 in communication with the processor 46. The output device 52 may be an external storage device or could also be a display device.

In addition, the control unit 42 a port 54 in communication with the processor 46. The port 54 may be any one of a number of different electronic ports, such as an Ethernet port, universal serial bus port, or any port capable of transmitting receiving electronic information. The port 54 may be in communication with the transmitter 22, receiver 24, or even the additional sensor 44.

Referring back to FIG. 1A, in this embodiment, the radiation 36a is reflected off the sheet dielectric sample 18a and sends as this as radiation 38a to the receiver 24a. However, it should be understood that the systems and methods disclosed in this application are equally applicable to transmitted radiation. Moreover, referring to FIG. 1B, disclosed is a system 10b that is similar to system 10a of FIG. 1A. Like reference numerals have been used to denote like components, with the only difference being that the reference numerals have the letter "b" after them in FIG. 1B instead of an "a" after them in FIG. 1A. The system 10b shows the transmitter 22b sending radiation 36b though the sample 18b. This radiation is transmitted though sample 18b and sent to receiver 24b as radiation 38b. Additionally, it should be understood that a system may incorporate the use of both transmitted and reflected radiation in a single system.

Figure 1B:
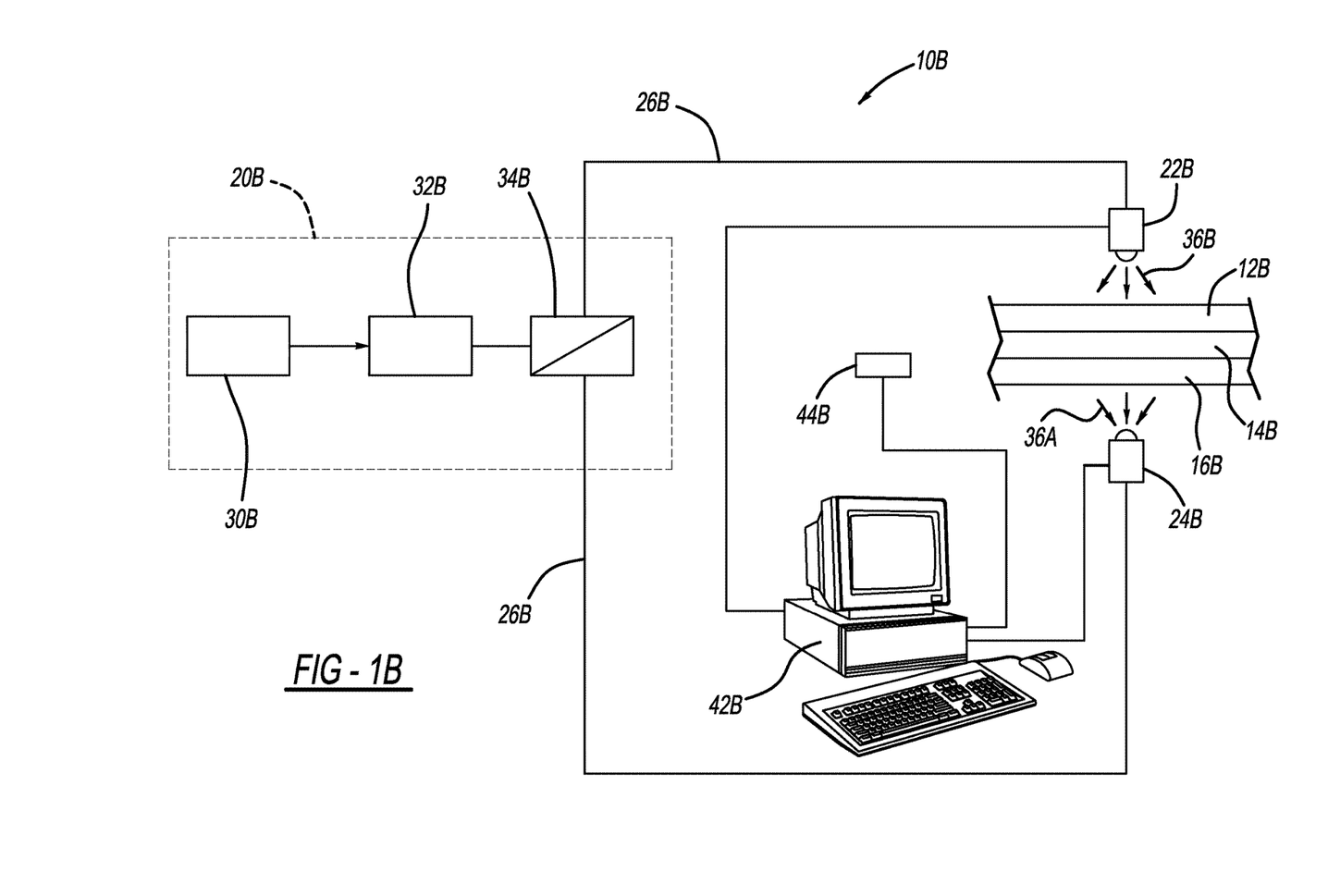
FIG. 1B illustrates a block diagram of a system for determining at least one property of a sheet dielectric sample using transmitted terahertz radiation.

Generally, the radiation 36a and 36b emitted from the transmitters 22a and 22b is terahertz radiation having a near single cycle electromagnetic impulse with time-domain Fourier components typically in the range of 0.050 terahertz to 3 terahertz. Usually the transmitter 22a emits the terahertz pulses in a sequential stream with a repetition rate between 50 MHz and 3 GHz, although lower and higher repetition rates are possible. Generally, the terahertz radiation utilized will be time-domain terahertz radiation. However this other types of bandwidth sources may be used including continuous wave and discrete bandwidth sources.

The samples 18a and 18b are identical, therefore only sample 18a will be described; however, the same description applies to sample 18b. The sample 18a has a first layer 12a, a second layer 14a, and a third layer 16a. It is also important to note that the sample 18a may have any one of a number of different layers or may be simple made from a single layer. One function of the system 10a is to sample the time-varying electric field as a function of time impinging on the receiver 24a as it has been generated by the transmitter 22a, propagated through the optical transport, and passing through and/or reflecting from the sample 18a under test. The time varying sampled recording of the electric field at the receiver 24a is usually called the "waveform". The waveform sampling is most readily accomplished by optically splitting the ultrafast laser source into two paths. The first path 26a goes the transmitter 22a and the second path 28a goes to the receiver 24a. The time of flight between the two paths is systematically changed by a variable optical delay line the delay line may be inserted in the first path 26a, the second path 28a, or both). The amount of variable delay is called the "waveform window". The receiver 24a is such that it only measures the electric field of the terahertz pulse synchronously with the ultrafast laser excitation pulse. The waveform measurement is essentially equivalent to a time varying gated integration of the electric field. The time varying optical delay may be achieved by linear or rotational opt-mechanical motion of mirrors and/or prisms; fiber stretching; repetition rate variance of the laser and substantially unequal optical path lengths; or asynchronously through the use of two lasers whose repetition rates are nearly the same but whose phase can be measured and/or controlled.

Like the transmitter 22a, the receiver 24a may be photoconductive semiconductor switch semiconductors or electro-optic crystal crystals. For a photoconductive semiconductor switch receiver 24a, the device is often microfabricated with a similar antenna to the transmitter 22a. However, instead of biasing the transmitter antenna, a voltage or current amplifier is connected to the antenna; and the output voltage or current is proportional to the magnitude (and sign) of the terahertz pulse electric field coincident in time with the receiver sampling ultrafast laser pulse. A receiver photoconductive semiconductor switch material ideally will have a (sub)-picosecond carrier lifetime. In addition to a (sub)-picosecond lifetime; the semiconductor material ideally has a very high resistivity so that the dark current is very low, like a photoconductive semiconductor switch receiver, and electro-optic crystal receiver is also sampled by the ultrafast laser pulse. However, instead of current or voltage being detected directly in the electro-optic crystal, the crystal serves to change the polarization state of the ultrafast laser pulse coincidently traveling through the electro-optic crystal with the terahertz pulse. The ultrafast laser pulse is analyzed by a polarizer followed by a photo-detector(s). The polarizer may be set to null the ultrafast laser transmission in the absence of a terahertz pulse; however more frequently the polarizer is set to balance the signal from two photodetecors measuring the orthogonal polarizations; and the signal difference between the photo-detectors is proportional to the sampled terahertz field.

Most rigorously, the propagation of the terahertz pulse through the experimental optical transport from the transmitter 22a to the receiver 24a can be modeled by Fourier Optics by the decomposition into a superposition of polarized plane waves with spatial wave vectors k and frequency components ω. Each of the sequential components of the optical transport contribute to the Transfer Function by altering each original Fourier component and serving as new emission point for one or more plane waves at certain points along the wave path (the Huygen's-Fresnel principle appropriate for plane waves, spherical waves, wavelets, etc.). Each component is summed at the receiver 24a (interfering at the receiver active area) and then back transferred in space (to compute the frequency dependent overlap of the active area) and in time (to compute the expected time varying electric field recorded as a waveform at the receiver 24a).

Typically the emission from the transmitter 22a is very nearly Gaussian, and the paraxial approximation holds. It should be noted, that because the frequency range of the terahertz pulse is so large, diffraction effects at lower frequencies may be much more substantial than at high frequencies. Propagation through apertures may act as a high pass filter for the terahertz pulses. Likewise, the terahertz pulses focused on the receiver 24a may be aligned to mode match decently at low frequencies by poorly at high frequencies, which acts as a low pass filter. Usually the terahertz optical transport is configured to confocally image the transmitter 22a onto the receiver 24a at unity magnification; and the diameter of the optics is chosen to be large enough not to result in any substantial loss of power at the lowest frequency of interest (often approximated by Pi times the Gaussian beam radius). As long as during the measurement process the frequency dependent spatial filtering effects are not changing, a reference reflection and/or transmission waveform can be used to normalize (in the frequency domain) or deconvolve (in the time domain) the measured waveform of the sample without the need to model or correct for most of the possible spatial effects on the amplitude or phase of the terahertz beam transmitting or reflection through each layer of the sample. In some cases, if the terahertz beam is undergoing a phase change due to focusing in the region where the sheet sample is located (Guoy phase shift) it may be necessary account for this phase shift in the propagation model.

While the description of the gauging method below often refers to a single layer thin sheet measured as "paper" as a heuristic example, it should be understood that the same analysis may be applied to determine the same physical parameters of any sheet dielectric sample 18a. As stated previously, the sheet material may have one or more layers, and be composed of one or more substances per layer.

Figure 3:
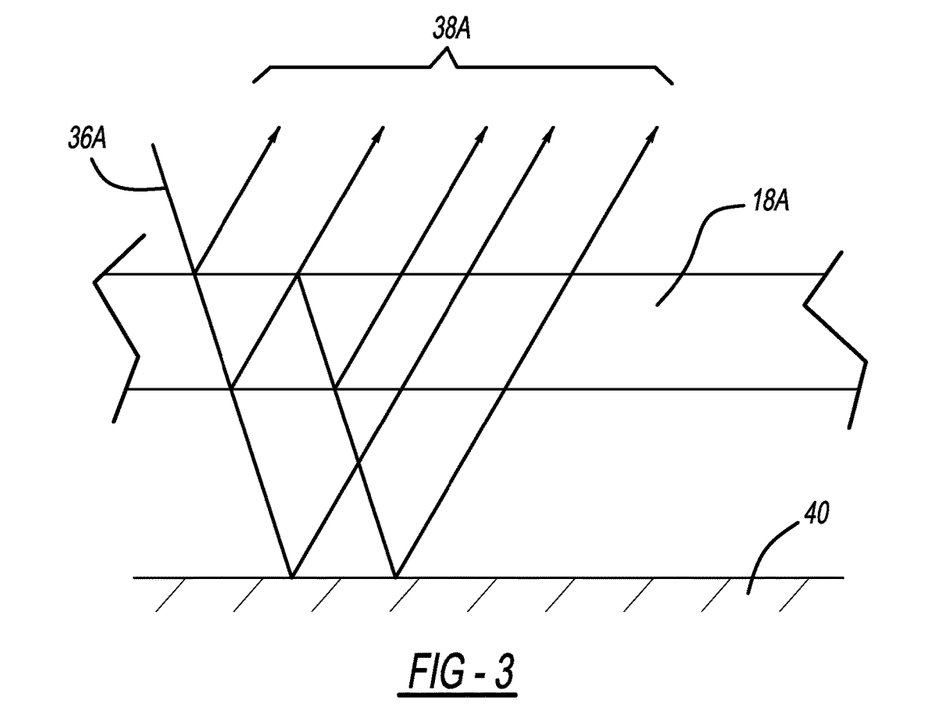
FIG. 3 illustrates a detailed view of a sample received terahertz radiation.

Referring to FIG. 3, FIG. 3 illustrates the sample 18a and the external reference structure 40. Here, radiation 36a provided by the transmitter 22a is directed towards the sample 18a. The sample 18a reflects portions of the radiation 36a. In addition, some of the radiation 36a passes through the sample 18a and is then reflected by the external reference structure 40. The reflected radiation 38a is a provided to the receiver 24a.

Figure 4:
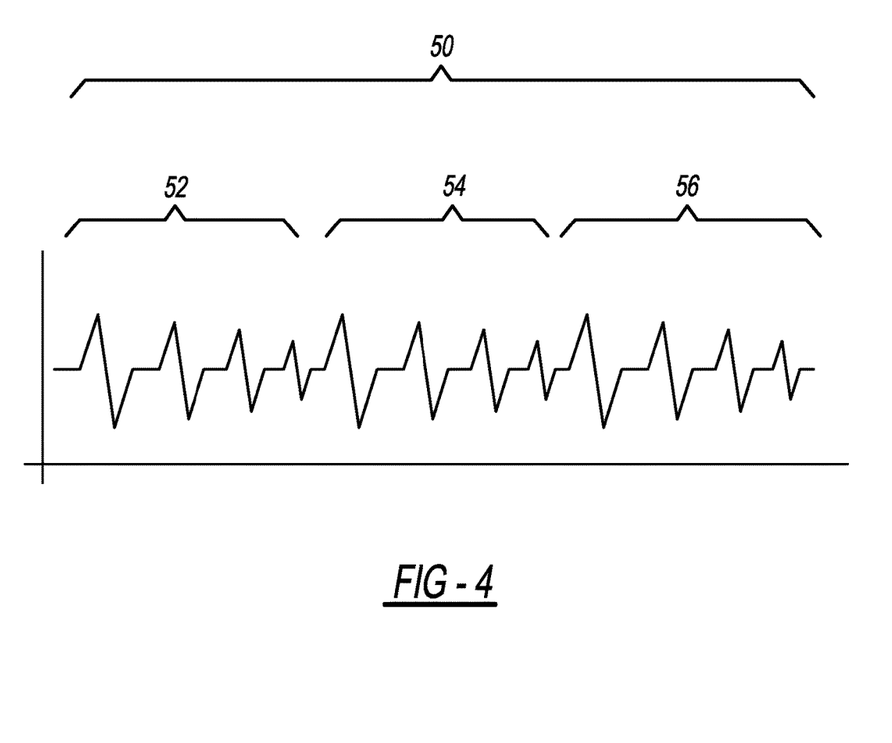
FIG. 4 illustrates a waveform generated from the sample of FIG. 3.

Referring to FIG. 4, the receiver 24A provides a waveform 50 to the control unit 42. The waveform 50 can be generally broken up into three separate regions 52, 54 and 56. Each region 52, 54, and 56 may represent different portions of radiation reflected from the sample 18A. For example, the first region 52 may represent portions of radiation reflected off the top surface of the sample 18A, the second region 54 may represent portions of radiation reflected off the bottom surface of sample 18A, and the third region 56 may represent portions of the radiation reflected off a rear reflector 40. In addition, it should be understood that each region 52, 54, and 56 may overlap include radiation from other regions. For example, region 54 may include some radiation from the surface of the sample 18A, while region 56 may include some radiation reflected off the bottom surface of the sample 18 A.

As stated before, the control unit 44A is in communication with the terahertz receiver 24a and configured to receive the measured waveform 50 from the terahertz receiver 24a. The control unit 42 is configured to choose at least one region 52, 54, and/or 56 of interest of the measured waveform 56. The control unit 42 then compares the at least one region of interest 52, 54, and/or 56 of the measured waveform 50 to a model waveform. Afterwards, control unit 42 then varies at least one parameter of a model waveform to minimize the difference between the model waveform and the measured waveform 50, and determines the at least one parameter of the model waveform so that the model waveform best matches the measured waveform 50. The control unit 42 may determine a best match of the measured waveform by minimizing the sum of the squares of the difference between the model waveform and the measured waveform 50.

The at least one parameter of the model waveform includes at least one of the following: thickness of a sheet dielectric model, complex index of refraction of a sheet dielectric model and/or a length of any layer of the sheet dielectric sample 18a and dimensions and optical constants of any optical element. The control unit 42 may also be configured to determine the thickness of the sheet dielectric sample 18a by the thickness of the model waveform to best match the measured waveform 50. The model waveform is derived from a reference waveform recorded when the sheet dielectric sample 18a is not present.

The complex index of refraction of the sheet dielectric model is a complex index of refraction of the model waveform is parameterized by water content and/or basis weight. As such, the control 42 may be configured to determine the water content or basis weight of the sheet dielectric sample by varying the complex index of refraction to predict a complex index of refraction of the sheet dielectric sample and utilize the predicted complex index of refraction to create the model waveform with additional parameters. The addition parameters may include a length of any layer of the sheet dielectric sample 18a and dimensions and optical constants of any optical element.

The control unit 42 may be further configured to transform the model waveform by a mathematical model based on optical physics of the propagation of the terahertz radiation through at least one known optical element that lies between the at least one terahertz transmitter 22a and the terahertz receiver 24a.

The terahertz receiver 24a may be configured to measure the polarization of the pulse of terahertz radiation and/or the angle of the beam of the pulse of terahertz radiation. From there, the control unit 42 may be further configured to determine at least one parameter measured of the measured waveform by additionally utilizing the polarization of the pulse of terahertz radiation and/or the angle of the beam of the pulse of terahertz radiation.

Further, the control unit 42 may also be configured to o determine at least one parameter measured of the measured waveform by additionally utilizing a distance of the sheet dielectric sample from a terahertz focusing lens and/or by additionally utilizing a distance of the sheet dielectric sample from a terahertz focusing lens and/or by additionally utilizing a determination of an empirical relation between the complex index of refraction with material change.

The transmitter 22a has optics such as mirrors and lenses to direct the terahertz pulses from the transmitter 22a, onto and/or through the sample 18a, and optics such as mirrors and lenses to collect the terahertz pulses transmitted and/or reflected from the sample 18a to one or more receiver 24a from which waveforms 50 are measured simultaneously or in sequence. The terahertz pulse beam 36a directed onto the sample 18a may be collimated or focused. Collimated beams will sample a larger area whereas focused beams will sample a smaller area. When focused, the sample 18a is usually at the focus of the beam; usually within the Rayleigh range compared to the thin paper, so that in effect the beam still can be treated as quasi-collimated as it transits through the thin paper. For both collimated and focused configurations the lenses (or off-axis parabolas or other focusing elements) will be configured in a "confocal" arrangement where the emission of the transmitter 22a is projected onto the receiver 24a with 1:1 magnification. This matches the mode of the transmitter 22a to the detection mode of the receiver 24a ideally and typically yields the best efficiency of detection and it typically results in the flattest frequency response as the extent to which the receiver 24a active area may act as a frequency dependent spatial filter is minimized. The terahertz beam 36a may be directed at normal incidence or at some non-zero angle of incidence. A sensor where the receiver 24a is configured to collect the reflected terahertz beam 38a at normal incidence is typically called a "co-linear" or "monostatic" configuration. A sensor where the receiver 24a is configured to collect the reflected terahertz beam 38a at non-zero angle of is typically called a "pitch-catch" or "bi-static" configuration. When configured in reflection, a high-numerical aperture confocal arrangement with the paper at the focus will improve the angular tolerance of the detection of the reflected beam if the paper flutters in angle, compared to a collimated beam (a specular reflection no-longer centered on the receiver 24a antenna may be detected less efficiently, and the antenna may act as a frequency dependent spatial filter). A co-linear configuration is less sensitive to vertical flutter of the paper spatially miss-directing the reflected beam; whereas a pitch-catch reflection may be badly miss-directed to the receiver 24a with vertical flutter.

A co-linear sensor may be constructed from independent transmitter 22a and receiver 24A modules using a partially transmitting and reflection beam combiner; or through the use of a polarization beam combiner. The beam combiners introduce loss; and a more efficient or convenient system can be constructed from a combined transmitter 22a and receiver 24A device with the same effective active area (the beam combiner is no longer required). Pitch-catch sensors require independent transmitter 22a and receiver 24A modules.

The waveform 50 should be adjusted so as to encompass all of the reflected and/or transmitted pulse energy from and/or through the sample 18a. Note that the measured energy within the window 50 is proportional to the integration of the square of the measured electric field comprising the raw-waveform. The waveform window 50 should be wide enough so that if the paper changes thickness and/or flutters all of the relevant Terahertz pulse energy remains in the window 50.

When the terahertz pulse beam 36a is directed onto the surface of the sample 18a a portion of the pulse beam 38a is reflected from each planar interface (for a single layer of a homogeneous paper sheet this is the top air-paper interface and the bottom paper-air interface); and a portion of the pulse beam transmits beyond each interface, as shown in FIG. 4.

The polarization of the terahertz beam may be controlled at the transmitter 22a and/or analyzed at the receiver 24a. This may be by rotating the axis of the linearly polarized transmitter 22a and/or receiver 24a antenna; and/or by placing a polarizer after the transmitter 22a and an analyzer prior to the receiver 24a. The polarization is typically measured with respect to the mirror plane of the paper; where the polarization parallel to the mirror plane is called "S" and the polarization in the propagation plane (at right angles to the mirror plane) is called "P". Note that for a zero angle of incidence the sense of polarization is degenerate. However the paper may have a small amount of bi-refringence or polarization dependent scattering so that the field measured with a cross-polarized receiver 24a may be non-zero.

The amount of electric field 38a reflected from each interface (as existing immediately at that interface) is a function of the electric-field Fresnel coefficients and equations. The Fresnel coefficients are a function of the incident angle, the polarization state (with regards to S and P in relation to the sample 18a) and the frequency complex dielectric constant of the sample 18a. The frequency dependent complex dielectric constant effects both the amplitude (real component) and phase (imaginary component); where the amplitude is related to the frequency dependent extinction coefficient and the phase is related to the frequency dependent index of refraction.

When the beam propagates to through the interface (air-sample 18a or sample 18a-air) it will refract. As it passes through the sample 18a, each of the Fourier frequency components will be changed in amplitude and intensity along the integrated path length through the sample 18a until the waveform hits the next interface; where it will then reflect and transmit via the Fresnel coefficients equations again.

Note that the each of the Fourier frequency components may reflect multiple times from the air-sample 18a and sample 18a-interfaces before exiting the sample 18a, which will be referred to as "paper" immediately below. The fields from each of the reflected components will in principle interfere. The (complex) Fourier frequency components of TD-Terahertz waveform collected in reflection geometry will be ordered as 1—[R air/paper]; 2—[T air/paper→T paper thickness t→R paper/air→Tpaper thickness t→T air/paper]; 3—[T air/paper→T paper thickness t→R paper/air→Tpaper thickness t→R paper/air→Tpaper thickness t→R paper/air→Tpaper thickness t→T air/paper]; etc. Note that reflection 1 has no internal passes through the paper;

reflection 2 has 2 internal passes through the paper; reflection 3 has 4 internal passes through the paper; etc. In this notation "T" means "transmits through" and "R" means "reflects from." Likewise the pulse sequence through the paper is 1—[T air/paper→T paper thickness t→T paper/air→]; 2—[T air/paper→T paper thickness t→R paper/air→Tpaper thickness t→R paper/air→Tpaper thickness t→T paper/air→]; etc. Note that transmission pulse 1 has 1 internal pass through the paper; transmission pulse 2 has 3 internal passes through the paper; etc.

The expected transmitted or reflected waveform can be modeled by Fourier transforming a reference pulse from the transmitter 22a and propagating the complex components through each of the sequence of reflections and transmissions to the receiver 24a as described by the sequence in the previous paragraph. The variable parameters are the thickness of the sample 18a, and the frequency dependent dielectric constant (including amplitude loss from the extinction coefficient and phase change from the index of refraction), angle of incidence, and the polarization of the transmitter 22a and receiver 24a. Each of the computed complex frequency domain Fourier components in this process may be added and then back-transformed into the time-domain to predict the time varying electric field as measured by the receiver 24a in either transmission, reflection, or both.

Note that in the time-domain a reflection from a high to low index will have the opposite sign with respect to a reflection from a low to high index. This can be useful to identify the sources of a pulse in a sequence if the sign of difference of index of refraction is known (which it is at the air-material interface). The low to high reflection is usually given a positive sign, although this is arbitrary.

The geometry of the sensor's terahertz optical path (angle of incidence; transmitter 22a and receiver 24a polarization) may be considered known constants (particularly if the paper is not fluttering substantially). The modeled waveform (summation of all Fourier components) can be fit to the actual transmission and/or reflection waveforms (individually or simultaneously) by a non-linear fitting routine which minimizes the residual (in the time or frequency domain) by varying the thickness and the parameters of a model for the frequency dependent extinction coefficient and frequency dependent index of the paper. Modeling the complex dielectric constant reduces the number of free parameters and constrains the fit to an empirically determined function. The frequency dependent extinction coefficient and index of refraction may usually be modeled by a slowly varying function of frequency. For example, in the absence of resonances, the extinction coefficient tends to be smaller at low frequencies, and often may be modeled by a quadratic (or other polynomial) function of frequency. In some cases it may be necessary to fit the data from multiple transmission and reflection waveforms from several different transmitter 22a polarizations, receiver 24a polarizations and angle of incidence.

This model may be extended to determine the characteristic parameters for a sheet material with multiple layers (for example, a paper with a coating). The pulse sequence calculation in transmission and reflection is constructed similarly to above, with each layer adding an additional Fresnel reflection interface and an additional frequency dependent complex dielectric constant model (frequency dependent extinction coefficient and frequency dependent index of refraction) and a layer thickness. Again, the model can be fit to measured transmission and/or reflection waveforms (which may be varied by angle of incidence and transmitter 22a and receiver 24a polarization) in order to determine all parameters corresponding to each layer.

The description of the model Terahertz pulse interaction with the sample 18a above assumes that transmission through the layer follows Beer's law; that is electric field decays exponentially as it traverses the uniform dielectric thickness. In practice, the transmission through a layer may experience an additional loss due to internal scattering of the field, and this loss may have to be modeled in order get accurate material parameter fits. This scattering loss may or may not follow Beer's law.

The description of the model terahertz pulse interaction with the sample 18a above assumes that reflection from the layers are described by the Fresnel coefficients and a specular reflection from a uniform optically smooth dielectric (note that the surface may be much rougher at terahertz frequencies than visible frequencies to be considered optically smooth). In practice the reflection interface may be rough and scatter a portion of the field, and this loss may have to be modeled in order get accurate material parameter fits.

Modeling the waveform to fit the physical parameters of the plastic from the transmitted and reflected waveforms may be simplified by certain approximations. The receiver 24a may be configured to capture the transmitted and (each of) the reflecting beam(s) and record the waveform simultaneously. If scattering is negligible then sum of the transmitted and reflected power (not field) may equal the input power minus the power lost to the frequency dependent extinction coefficient. If the frequency dependent loss is negligible, and the frequency dependent index of refraction is constant then the transmitted pulse waveform is only reduced in amplitude by propagating through the material (it does not change shape).

Furthermore, if the thickness of a layer of sample 18a is large compared to the longest wavelength in the terahertz pulse then the time-domain waveform of a reflected pulse will have each pulse in sequence well separated so that the interference between pulses may be ignored. In this case, the thickness of the material for any particular sequence is proportional to the group velocity/2 times the measured time flight between the reflection pulses from the upper and lower interfaces of the layer. As long as the material composition and density remains constant, the thickness of the material can be derived from this time of flight (and because the density is constant, so can basis weight). The time of flight between pulses in the waveform can be determined by deconvolution and model fitting to a reference pulse.

In many measurement cases (especially paper) the sheet material may be thin compared to the longest wavelength of interest in the reflected pulse. In this case the peak reflected pulses will change in amplitude and time with respect to the ideal time of flight for thickness. This is also known as a Fabry Perot etalon effect. The time of flight cannot be determined by a simple peak find or fit to a pulse shape such as a Gaussian or Lorentizian; rather the field of the modeled peaks may be summed so that the interference can be taken into account.

In transmission, as long as the material composition is uniform and the density does not change (and absorption and dispersion effects are negligible), the thickness is proportional to [time of flight of the pulse when the sheet is present minus time of flight in air alone] times [group velocity of material minus group velocity in air]. The timing of the transmitted pulse is not meaningfully distorted by a variable etalon effect of thin sheet. The reference time flight when the sample is not present may not drift. This may require the distance between the transmitter 22a may receiver 24a either be stabilized or the time of flight corrected by an instrument not sensitive to the presence of the paper (for example a magnetic or eddy current distance gauge). If the drift is very slow the sensor may periodically move "off web" to collect a new reference waveform (and time of flight).

Reflection configurations are often more convenient than transmission measurements where the receiver 24a is placed on the opposite side of the sheet from the transmitter 22a. For example, a gantry system may require two synchronized motion stages. A measurement in reflection for which the timing or amplitude to first order is not distorted by the thin sheet etalon effect can be made by placing a reflection plane (such as a metal mirror or rail) behind the sheet so that strong pulse reflects back through the sheet (passing through it a second time) to the receiver 24a. In this case the thickness is proportional to [time of flight of the pulse when the sheet is present minus time of flight in air alone]/2 times [group velocity of material minus group velocity in air]. The reference time flight when the sample is not present may not drift. The distance between the transmitter 22a/receiver 24a pair to the reflection plane may either be stabilized or the time of flight corrected by an instrument not sensitive to the presence of the paper (for example a magnetic or eddy current distance gauge). If the drift is very slow the sensor may periodically move "off web" to collect a new reference waveform (and time of flight).

The reflection gauge configuration may be further improved by placing a slightly reflecting window above the sheet (as well as the reflection mirror below the sheet). The window may be made of a terahertz transparent plastic (HDPE) or glass (fused silica), for example. This is known as the "External Reference Structure" or ERS. The reference time flight when the sample is not present may not drift. The distance between the inside surface of the window to the reflection plane may either be stabilized or the time of flight corrected by an instrument not sensitive to the presence of the paper (for example a magnetic or eddy current distance gauge). If the drift is very slow the sensor may periodically move "off web" to collect a new reference waveform (and time of flight).

Note that moving off web is not always possible. When an external reference structure 40 is used, the following time of flights can be measured from the pulse sequence (with a single layer sheet): (1) inside window to sample top; (2) sample top to sample bottom; and (3) sample bottom to reflection plane. The distances of (1)+(3) can be computed using the speed of light in air. The caliper thickness of the sheet is equal to the known (stabilized and/or periodically measured) distance between the inside external reference structure 40 window and the reflection plane minus [distances (1)+(3)]. This is a true caliber thickness as it is independent of the index of refraction of the sheet. The group velocity of the sheet can be calculated by dividing the caliper thickness by the time of flight (2). By using an external reference structure 40, the terahertz system can measure both the true caliper thickness, basis weight and density of the sheet (assuming the composition stays the same and the density variation is due to something like incorporated airspace, such as foam).

In many cases, however, the sheet absorbs enough such that the pulses transmitting through the sheet are distorted (usually lengthened and loss of amplitude due to loss of higher frequencies). In this case approximations of constant frequency dependent extinction and/or index of refraction may not be made, and the thickness and complex dielectric constant model parameters may be fit simultaneously using the scheme of the full model described above (possibly including scatter loss). This can be done in pure reflection, in transmission, with a reflection plane, or external reference structure 40.

An important physical parameter of paper (and other sheets) to be measured on or off-line is the percentage of water incorporated in the total mass of the paper. Water (via exposure to humidity or liquid from pulp prior to drying) may be incorporated in the interstitial space between the paper fibers; and/or bound to the fibers. This will modify the complex dielectric constant of the paper (both frequency dependent index of refraction and frequency dependent extinction coefficient) as a function of water basis weight. In addition, the frequency dependent scattering may change as a function of water basis weight. The thickness of the paper may change as a function of water basis weight. The frequency dependent index of refraction (related to the group velocity) through the moist paper may be better modeled independently from the index of refraction for the moist paper use to calculate the Fresnel coefficients.

Simple amplitude (or squared amplitude) measurements of fitted pulses may not be directly proportional to the concentration of water as might be expected by Beers Law due to the complexity of the physics of the incorporation of the water. Most notably, the effect of interstitial water and adsorbed bound water to both the index of refraction and the extinction coefficient vs. water basis weight may not follow Beer's Law as a function of concentration. The measured of the reflection pulse amplitudes, in particular the transmitted pulses, will be modified by not only internal extinction due to water but also increased or decreased amplitude due to preceding reflection pulses changing due to the Fresnel coefficients being a function of the water basis weight.

The thickness, and of the frequency dependent coefficients in the propagation model can be measured empirically by fitting one or more of the reflection or transmission configuration waveforms independently or simultaneously as a function known water basis weight. This measurement configuration may be aided by the use of an ERS. The empirically derived family of curves can then be used to fit the water basis weight (percentage) of a sample of paper with unknown water concentration.

Note that the effect of the Fresnel coefficient changes as function of angle and polarization. Waveforms may be collected at multiple angles and polarization combinations. A particular useful configuration may be a Brewster's angle configuration. At Brewster's angle the Fresnel coefficients are 0 and the "P" polarized pulse transmits with no frequency dependent loss, except for the frequency dependent extinction coefficient. Measurements using Brewster's angle may be made in true transmission or with an ERS/reflection sensor configuration tilted at the correct angle with respect to the paper. Brewster's angle measurements can be particularly useful when the water concentration, and additional loss, is small compared to the background of the paper Fresnel reflections.

As discussed previously, the frequency dependent extinction coefficient (and/or index of refraction) may be empirically modeled by a simple function with a few parameters such as a polynomial. Like most dielectrics, water absorbs more strongly at higher terahertz frequencies compared to lower terahertz frequencies. The slope or curve of the frequency dependence is a much steeper for water than paper. Fitting of the complete waveform (all reflection and transmission components) can determine the (polynomial) parameters of the frequency dependence. These frequency dependent parameters may have a comparatively simple (proportional) relationship to water basis weight. In certain cases, more simple Fourier analysis of transmitted pulses, and the measurement of caliper, could be used to compute the empirical frequency dependent parameters more efficiently than fitting to the full model of propagation.

The following is a calculation of the amplitude of three primary reflections assuming constant frequency independent index of refraction, constant frequency dependent extinction coefficient, and Beer's law. This is a significant approximation, and should not be considered to represent all experimental cases of water absorption, where the more complete modeling of pulse propagation described above may be more appropriate.

A monostatic (co-linear) THz reflection measurement is made with the incident pulse traveling left to right through a sheet of material $18a$, reflecting from a 100% reflecting external reference structure 40, back through the sheet $18a$, and into the receiver $24a$. This results in 3 primary reflections.

The surfaces of the sheet $18a$ and the external reference structure 40 are aligned normal to the incident beam such that the interface reflections travel directly back to the receiver $24a$. The terahertz optics are configured such that each of the interface reflections are mode matched with the receiver $24a$ regardless of distance along the axis of propagation and 100% of the electric field from each interface is recorded. If not, some method for correcting the loss of efficiency as a function of position along the axis of propagation may be made.

The power of each reflected pulse can be found by integrating the square of the electric field over a fixed duration and then dividing by that duration. This requires the pulses to be sufficiently well separated in time such that the fields from each pulse do not interfere. Alternatively, each of the reflected pulses can be deconvolved with a metal reference, and the peak power is proportional to the amplitude squared.

There is no accounting for any frequency dependent change in the complex index of refraction (change in index or extinction coefficient with frequency) or for Fabry-Perot effects. The interface reflection coefficient $R_e$ is the same going from air-material and material-air.

However for this method we assume that upon adsorption of water both the internal transmission AND the reflection coefficients are not necessarily equal to the pure dry state. That is, $T_i \neq T_{i+w}$, AND $R_e \neq R_{e+w}$. The caliper dimensions of the material do not change substantially upon absorption of water.

Definitions $I_0$ power (not field) of incident pulse
$T_i$ power internal transmission of sheet material ($0 \leq T_i \leq 1$)
$L_i$ length of sheet (measured by THz caliper, for example)
$R_e=1-T_e$ power reflection from air/sheet interface
$T_e=1-R_e$ power transmission through air/sheet interface
$I_1$ pulse power reflected from first air-material interface
$I_2$ pulse power reflected through second material-air interface and back through the material
$I_3$ pulse power reflected from mirror, having travelled twice through the material
$\alpha_i$ extinction coefficient of material
$\alpha_w(c_w)$ concentration dependent extinction coefficient of water
$c_w(\alpha_w)$ concentration of water vs. extinction coefficient of water
$T_{i+w}$ power internal transmission of sheet plus water Using the external reference structure 40 and suitable method for determining the power reflected from each interface, measure the following reflected pulse powers:

$$I_1 = I_0(1-T_e) \qquad (1)$$

$$I_2 = I_0(1-T_e)T_e^2 T_i^2 \qquad (2)$$

$$I_3 = I_0 T_e^4 T_i^2 \qquad (3)$$

Then we can solve first for $T_e$ $$T_e = -I_3/I_2 + \mathrm{SQRT}((I_3/I_2)^2 + 4I_3/I_2) \qquad (4)$$

Knowing $T_e$ we can solve for $T_i$ $$T_i = \mathrm{SQRT}((I_3/I_2)(1-T_e)/T_e^4) \qquad (5)$$

In terms of the extinction coefficient $\alpha_i$ for the pure material, using Beer's law, $$T_i = \exp(-\alpha_i L_i) \qquad (6)$$

$$\alpha_i = -\ln(T_i)/L_i \qquad (7)$$

While the present invention has been described in terms of certain preferred embodiments it will be understood that the invention is not limited to this disclosed embodiments as those having skill in the art may make various modifications without departing from the scope of the following claims and equivalents thereof.

The invention claimed is:

1. A system for determining at least one property of a sheet dielectric sample using terahertz radiation, the system comprising:

at least one terahertz transmitter configured to output a pulse of terahertz radiation to the sheet dielectric sample;

a terahertz receiver configured to receive at least a portion of the pulse of terahertz radiation from the sheet dielectric sample, wherein the terahertz receiver is configured to output a measured waveform based on the terahertz radiation received by the terahertz receiver;

a control unit in communication with the terahertz receiver and configured to receive the measured waveform from the terahertz receiver;

wherein the control unit is configured to:

choose at least one region of interest of the measured waveform, compare the at least one region of interest of the measured waveform to a model waveform, wherein the model waveform is derived from a reference waveform recorded when the sheet dielectric sample is not present, vary at least one parameter of a model waveform to minimize the difference between the model waveform and the measured waveform, determine the at least one parameter of the model waveform so that the model waveform best matches the measured waveform, and wherein the at least one parameter of the model waveform includes at least one of the following: thickness of a sheet dielectric model and complex index of refraction of a sheet dielectric model.

2. The system of claim 1, wherein the control unit is configured to determine the thickness of the sheet dielectric sample by the thickness of the model waveform to best match the measured waveform.

3. The system of claim 1, wherein the complex index of refraction of the sheet dielectric model is a complex index of refraction of the model waveform is parameterized by water content and/or basis weight.

4. The system of claim 3, wherein the control unit is configured to:
determine the water content or basis weight of the sheet dielectric sample by varying the complex index of refraction to predict a complex index of refraction of the sheet dielectric sample
utilize the predicted complex index of refraction to create the model waveform with additional parameters.

5. The system of claim 4, wherein the addition parameters include a length of any layer of the sheet dielectric sample and dimensions and optical constants of any optical element.

6. The system of claim 1, wherein the portion of the pulse of terahertz radiation received by the terahertz receiver from the sheet dielectric sample is reflected by the sheet dielectric sample to the terahertz receiver.

7. The system of claim 6, further comprising a mirror configured to reflect terahertz radiation emitted by the terahertz transmitter to the terahertz receiver.

8. The system of claim 7, wherein the at least one parameter of the model waveform includes a distance from the mirror to a reference pulse.

9. The system of claim 1, wherein the waveform is a time domain waveform.

10. The system of claim 1, wherein the waveform is a frequency domain waveform.

11. The system of claim 1, wherein the control unit is configured to transform the model waveform by a mathematical model based on optical physics of the propagation of the terahertz radiation through at least one known optical element that lies between the at least one terahertz transmitter and the terahertz receiver.

12. The system of claim 1, wherein the control unit determines a best match of the measured waveform by minimizing the sum of the squares of the difference between the model waveform and the measured waveform.

13. The system of claim 1, further comprising at least one additional sensor for sensing properties of the sheet dielectric sample.

14. The system of claim 13, wherein the at least one additional sensor includes at least one of a near infrared sensor, an eddy current sensor, a magnetic sensor, a visible spectroscopy sensor, calipers, a nuclear magnetic resonance spectroscopy sensor, or a Raman spectroscopy sensor.

15. The system of claim 1, wherein:
the terahertz receiver is configured to measure the polarization of the pulse of terahertz radiation; and
the control unit is configured to determine at least one parameter measured of the measured waveform by additionally utilizing the polarization of the pulse of terahertz radiation.

16. The system of claim 1, wherein:
the terahertz receiver is configured to measure the angle of the beam of the pulse of terahertz radiation; and
the control unit is configured to determine at least one parameter measured of the measured waveform by additionally utilizing the angle of the beam of the pulse of terahertz radiation.

17. The system of claim 1, wherein the control unit is configured to determine at least one parameter measured of the measured waveform by additionally utilizing a distance of the sheet dielectric sample from a terahertz focusing lens.

18. The system of claim 1, wherein the control unit is configured to determine at least one parameter measured of the measured waveform by additionally utilizing a determination of an empirical relation between the complex index of refraction with material change.

* * * * *